United States Patent
Chin et al.

(10) Patent No.: US 11,052,119 B2
(45) Date of Patent: Jul. 6, 2021

(54) CELL-BASED COMPOSITION AND USE THEREOF FOR TREATMENT OF DIABETES AND ASSOCIATED METABOLIC DISORDERS AND FOR AMELIORATION OF INSULIN RESISTANCE IN PRE-DIABETES

(71) Applicant: Cytopeutics Sdn. Bhd., Selangor (MY)

(72) Inventors: Bernard Sze-Piaw Chin, Selangor (MY); Kong Yong Then, Selangor (MY); Soon Keng Cheong, Selangor (MY)

(73) Assignee: Cytopeutics Sdn. Bhd., Selangor (MY)

( * ) Notice: Subject to any disclaimer, the term of this patent is extended or adjusted under 35 U.S.C. 154(b) by 177 days.

(21) Appl. No.: 16/284,177

(22) Filed: Feb. 25, 2019

(65) Prior Publication Data

US 2019/0209620 A1  Jul. 11, 2019

Related U.S. Application Data

(62) Division of application No. 15/597,725, filed on May 17, 2017, now abandoned.

(30) Foreign Application Priority Data

May 25, 2016  (MY) ........................ PI 2016701900

(51) Int. Cl.
*A61K 35/28* (2015.01)
*C12N 5/0775* (2010.01)

(52) U.S. Cl.
CPC ............ *A61K 35/28* (2013.01); *C12N 5/0665* (2013.01)

(58) Field of Classification Search
None
See application file for complete search history.

(56) References Cited

U.S. PATENT DOCUMENTS

| 2007/0269887 A1 | 11/2007 | Coelho et al. |
| 2012/0201791 A1 | 8/2012 | Yoo |
| 2015/0086514 A1* | 3/2015 | Huang ............... A61P 3/10 424/93.7 |

OTHER PUBLICATIONS

Cortes, D. Orbegozo; et al; "Isotonic crystalloid solutions: a structured review of the literature" British Journal of Aneaesthesia, 112, 968-981, 2014 (Year: 2014).*

Jong, Renate de; "Advanced Cell-Based Cardiac Repair: How to Mend a Broken Heart" Thesis, Erasmus University Medical Center, 2014 (Year: 2014).*

Al-Saqi et al "Defined Serum- and Xeno-Free Cryopreservation of Mesenchymal Stem Cells" Cell Tissue Bank vol. 16, pp. 181-193, 2015.

Chhabra et al "Challenges in the Management of Type 2 Diabetes Mellitus and Cardiovascular Risk Factors in Obese Subjects: What is the Evidence and What are the Myths?" International Journal of Endocrinology vol. 2013, pp. 1-10, 2013.

(Continued)

*Primary Examiner* — David W Berke-Schlessel
(74) *Attorney, Agent, or Firm* — Cesari & McKenna, LLP (57) ABSTRACT

The present invention relates to a cell-based composition comprising a suspension of mesenchymal stem cells in crystalloid with a cellular concentration from 0.01 million to 3.0 million cells/ml. The cell-based composition is used in a form of medicament for treatment of diabetes and its associated metabolic disorders and complications.

16 Claims, 5 Drawing Sheets

(56) References Cited

OTHER PUBLICATIONS

Dominici et al "Minimal Crtieria for Defining Multipotent Mesenchymal Stromal Cells: The International Society for Cellular Therapy Position Statement" Cytotherapy vol. 8, pp. 315-317, 2006.
Han et al "Metabolic Syndrome" Medicine vol. 39, pp. 24-31, 2010.
Kode et al "Mesenchymal Stem Cells: Immunobiology and Role in Immunomodulation and Tissue Regeneration" Cytotherapy vol. 2009, pp. 377-391, 2009.
Ma et al "Immunobiology of Mesenchymal Stem Cells" Cell Death and Differentiation vol. 21, pp. 216-225, 2014.
Rhodes et al "Molecular Insights Into Insulin Action and Secretion" European Journal of Clinical Investigation vol. 32, pp. 3-13, 2002.
Xin et al "Insulin-Producing Cells Differentiated from Human Bone Marrow Mesenchymal Stem Cells *In Vitro* Ameliorate Streptozotocin-Induced Diabetic Hyperglycemia" PLoS One vol. 11, pp. 1-17, 2016.

* cited by examiner

Adipogenesis

Chondrogenesis

Osteogenesis

CELL-BASED COMPOSITION AND USE THEREOF FOR TREATMENT OF DIABETES AND ASSOCIATED METABOLIC DISORDERS AND FOR AMELIORATION OF INSULIN RESISTANCE IN PRE-DIABETES

CROSS-REFERENCE TO RELATED APPLICATIONS

The present application is a divisional of U.S. application Ser. No. 15/597,725, filed May 17, 2017, which claims the priority of Malaysian Application No. PI 2016701900, filed on May 25, 2016. The contents of these prior applications are hereby incorporated by reference in their entirety.

FIELD OF THE INVENTION

The present invention relates to a cell-based composition and use thereof for treatment of diabetes and its metabolic disorders and complications associated with this disease and for amelioration of insulin resistance in pre-diabetes.

BACKGROUND OF THE INVENTION

Diabetes mellitus is a debilitating disease which affects 180 million people worldwide. In 2016, World Health Organization (WHO) reported that diabetes mellitus affects nearly one in 11 adults.

It can be classified into two categories, type I diabetes which is previously known as insulin dependent or juvenile onset, and type II diabetes, also known previously known as non-insulin dependent or adult onset. A recent surge in predominantly type II diabetes is largely due to poor lifestyle and habits.

Diabetes is a metabolic disease characterised by hyperglycemia which refers to rising blood glucose level, caused by deteriorating insulin signalling due to insulin resistance and pancreatic β-cell dysfunction (Rhodes et al., 2002). Insulin resistance is characterised by increased serum insulin and eventually insulin depletion. Initial increased insulin state results in an increase in inflammation, cholesterol and fatty liver infiltration prior to overt clinical diabetes. Insulin resistance and hyperinsulinemic states could increase catecholamine activity, hence, causing hypertension in diabetic patients and inflammation which inhibit cholesterol esterification (Han et al., 2011). Clinical manifestations resulting from diabetic state include nephropathy, dyslipidaemia, diabetes foot ulcer, macular oedema, cardiomyopathy and stroke, among others.

In efforts to treat diabetes, various treatment methods have been developed in the past. Conventionally, management of uncontrolled diabetes is carried out by means of dramatic alteration in lifestyle and diet, medication and insulin therapy. In some cases, obese patients afflicted with uncontrolled diabetes were required to undergo bariatric surgery. Chhabra et al. (2013) reported that although these methods have been demonstrated to confer overall health benefits, however, it is understood that the effects of these methods on remission of pre-existing diabetes mellitus and reduction in cardiovascular risk remain inconsistent. Meanwhile, one of the common ways to treat insulin resistance is medication using insulin sensitizers. Although medication may improve hyperglycaemia or temporarily resolve response to insulin in target tissues, however, it was found to be less effective at impeding progressive dysfunction of insulin-producing cells which are present in pre-diabetics.

In light of the above, medical experts have begun to look into other ways for treating diabetes and for ameliorating insulin resistance in pre-diabetes which are safer, non-invasive and clinically effective. Studies on mesenchymal stem cells, also known as mesenchymal stromal cells, have generated a lot of interest among researchers and clinicians due to its attributes which include ability of differentiating into insulin-producing cells and immunoprivilaged properties which eliminate risk of rejection. Mesenchymal stem cells possess an ability to differentiate into specialised cells which enables regeneration of new tissues and repair of damaged or defect tissues in the body. In 2014, Ma et al. reported that mesenchymal stem cells are devoid of ethical, teratomas-formation and histocompatibility issues. As such, mesenchymal stem cells have become focus of research investigation amongst medical experts to seek suitable protocols for treatment of diseases. In 2016, Xin et al. demonstrated that mesenchymal stem cells transplantation is able to ameliorate diabetic hyperglycaemia in mice. Apart from differentiation ability into insulin producing cells, advances in research demonstrate that mesenchymal stem cells possess an immuno-modulatory ability.

Therefore it is postulated that mesenchymal stem cells might be able to contribute to recovery of pancreatic beta-islet cell dysfunction and skeletal muscle insulin receptor dysfunction in pre-diabetics, motivating inventors of the present invention to successfully develop a novel cell-based composition which is clinically safe and therapeutically effective for treatment of diabetes and its metabolic disorders and for ameliorating insulin resistance in pre-diabetes.

SUMMARY OF THE INVENTION

In alleviating limitations resulting from conventional methods in the past, the present invention provides a cell-based preparation and use thereof which is clinically safe and therapeutically effective for treatment of diabetes and its associated metabolic disorders and complications and for amelioration of insulin resistance in pre-diabetes.

More particularly, the present invention relates to a cell-based composition comprising a suspension of mesenchymal stem cells in crystalloid with a cellular concentration from 0.01 million to 3.0 million cells/ml wherein the cell-based composition is used in a form of medicament for treatment of diabetes and its associated metabolic disorders and complications selected from a group including nephropathy, dyslipidaemia, diabetes foot ulcer, macular oedema, cardiomyopathy or stroke and for amelioration of insulin resistance in pre-diabetes.

Thus, one aspect of this invention is a method for treating diabetes and its associated metabolic disorders and complications and for ameliorating insulin resistance in pre-diabetes in a subject by administering to the subject (e.g., by intravenous infusion carried out for 0.5 to 2 hours) the cell-based composition described above and hereinafter in a therapeutically effective amount (e.g., 0.25 million to 3.0 million cells/kg body weight).

BRIEF DESCRIPTION OF DRAWINGS

The drawings constitute part of this specification and include an exemplary or preferred embodiment of the invention, which may be embodied in various forms. It should be understood, however, that the disclosed preferred embodiments are merely exemplary of the invention. Therefore the figures disclosed herein are not to be interpreted as limiting, but merely as the basis for teaching one skilled in the art of the invention.

In the appended drawings.

DETAILED DESCRIPTION OF THE INVENTION

A detailed description of the present invention is described herein. The present invention is directed to a cell-based composition and use thereof for treating diabetes and complications arising from this condition. More particularly, the present invention relates to a cell-based composition comprising a suspension of mesenchymal stem cells in crystalloid with a cellular concentration from 0.01 million to 3.0 million cells/ml wherein the cell-based composition is used in a form of medicament for treatment of diabetes and its associated metabolic disorders and complications selected from a group including nephropathy, dyslipidaemia, diabetes foot ulcer, macular oedema, cardiomyopathy or stroke and for amelioration of insulin resistance in pre-diabetes.

In a preferred embodiment of the present invention, accordingly, the mesenchymal stem cells used for preparation of the suspension are derived from various sources including, but not limiting to, human umbilical cord, bone marrow, fat tissue, peripheral blood or tooth pulp. Samples are either collected from mothers post-birth or from healthy donors. If required, the samples are cleaned and disinfected accordingly.

Upon collection, the samples are sent to laboratory to be processed further. The samples will be digested using a digestion enzyme, preferably, but not limiting to collagenase type II and followed by centrifugation, leaving a layer of supernatant and pellet containing mesenchymal stem cells. The mesenchymal stem cells are isolated and cultured in a specially formulated medium supplemented with a combination of various antibiotics and animal-free serum. The cultures are maintained at a temperature range from 35° C. to 40° C., preferably at 37° C. in a humidified atmosphere for 3-4 days.

As it will be apparent to a person of ordinary skill in the art, mesenchymal stem cells are adherent to plastic. Non-adherent cells are discarded and the growth medium is replaced every 3-4 days until the cells reached confluence.

Upon reaching 70%-80% confluence, the adherent mesenchymal stem cells are incubated with a dissociation enzyme, preferably, but not limiting to trypsin and re-plated at $1\times10^4$ cells/ml for a series of passages, preferably, but not limiting to 3-4 passages. The mesenchymal stem cells are then harvested in a culture flasks, thus expanding population of the cells.

The mesenchymal stem cells are characterized in accordance to a criteria set forth by International Society for Cellular Therapy (ISCT). Apart from adherence to plastic, established criteria defining mesenchymal stem cells include expression of antigen markers as measured by flow cytometry and tri-differentiation ability of the cells (Dominici 2006). Using flow cytometry, the mesenchymal stem cells are defined by expression of CD73, CD90, and CD105 markers whilst absence of expression for CD34, CD45, and HLA-DR markers. Meanwhile, the tri-differentiation ability of the mesenchymal stem cells is demonstrated by way of the cells differentiating into osteoblasts, adipocytes and chondroblasts.

Once the population of mesenchymal stem cells have been expanded, a disassociation enzyme, preferably, but not limiting to trypsin is added in to the flasks and incubated at a temperature range from 35° C. to 40° C., more preferably at 37° C., for a period of 1-15 minutes, more preferably for 5 minutes to detach the plastic-adherent mesenchymal stem cells, leaving the cells slightly shrunk. Next, the flasks are gently tapped to dislodge the cells and medium is further added to dilute the trypsin, forming a mesenchymal cell suspension. The cell suspension is then transferred into 50 ml centrifuge tubes and centrifuged at a speed range from 300 g to 800 g, more preferably at 500 g at a temperature range from 18° C. to 20° C. for 10 minutes forming a layer of supernatant with pellet at bottom of the tubes. The supernatant is removed, leaving the pellet of mesenchymal stem cells in the tubes.

The pellet of mesenchymal stem cells are re-suspended in a sterile cryovial of 1.8 ml in size containing cryopreservation medium comprising from 80% to 90% animal-free serum and a cryoprotectant, preferably, but not limiting to dimethyl sulfoxide from 1% to 10%. Alternatively, dimethyl sulfoxide may also be substituted with human serum albumin. Typically, a cryovial contains from 25 million to 30 million cells per vial. Alternatively, cryovials of up to 5 ml in size may also be used.

The mesenchymal stem cells in cryovials are frozen in a controlled rate freezer until −70 to −90° C. but preferably −90 gradually before transferring into quarantine tank, preferably, but not limiting to a vapour phase liquid nitrogen storage tank.

To prepare a cell-based composition for the treatment of diabetes and its metabolic disorders and complications associated with and for amelioration of insulin resistance in pre-diabetes, the cryopreserved mesenchymal stem cells in cryovials are first thawed at a temperature ranging from 30° C. to 40° C., preferably at 37° C. in a water bath or an incubator for a period from 1 to 5 minutes, more preferably at 2 minutes. Next, the cells are then transferred into new sterile cryovials and are washed with sterile saline, preferably but not limiting to 0.9% sodium chloride. The washed cells in the sterile cryovials will then be centrifuged at a speed ranging from 500×g to 1000×g, preferably at 800×g for a period from 3 to 10 minutes, more preferably for 5 minutes at room temperature, forming a layer of supernatant and a pellet of mesenchymal stem cells.

Typically, the supernatant is removed and discarded, leaving the pellet of mesenchymal stem cells in the cryovial. In one preferred embodiment of the present invention, the pellet of mesenchymal stem cells are then re-suspended with sterile saline at a volume ranging from 5 to 20 ml, preferably at 10 ml, forming a suspension of mesenchymal stem cells.

In another preferred embodiment of the present invention, a cell-based composition is prepared by infusing the suspension of mesenchymal stem cells into crystalloid to reach a cellular concentration from 0.01 million to 3.0 million cells/ml. The crystalloid includes, but not limiting to normal or half-normal saline or colloid.

Exact amount of cells per kg body weight to be administered into a patient depends on variety of factors including body weight, route of administration, age and gender of the patient, and also the type of mechanism of action targeted. Typically, the therapeutically effective amount of the cell-based composition used for the treatment of diabetes and its metabolic disorders and complications associated with and for amelioration of insulin resistance in pre-diabetes is from to 0.25 million to 3.0 million cells/kg body weight.

Measurement of glycated haemoglobin A1c, commonly known as HbA1c, is employed in a screening test to pick up diabetes.

HbA1c can indicate patients with pre-diabetes or diabetes as follows:

| HbA1c | mmol/mol | % |
| --- | --- | --- |
| Normal | Below 42 mmol/mol | Below 6.0% |
| Pre-diabetes | 42 to 47 mmol/mol | 6.0% to 6.4% |
| Diabetes | 48 mmol/mol or over | 6.5% or over |

Source: diabetes.co.uk

In the present invention, the HbA1c to aim for in qualifying patients with diabetes is ≥6%.

Other parameters to be assessed for diagnosis of metabolic disorders in diabetes patients include creatinine (marker of renal impairment and nephropathy) and lipid profile comprising total cholesterol and low-density lipoprotein (LDL) (markers of dyslipidaemia).

The following examples further illustrate but by no means limit the scope of the invention:

Example 1: Collection and Handling of Umbilical Cord Sample

The umbilical cord sample was detached from placenta of a donor post-birth using medical scissors and was immediately submerged in povidone iodine solution for 1-5 minutes to eliminate bacteria and to avoid any risk of contamination. Alternatively, the umbilical may be disinfected using alcohol swab. Upon disinfection, the umbilical cord was then placed in a sterile container of sterile saline solution to maintain moisture. Subsequently, the sterile container was placed into a collection kit and was transported to laboratory using a thermo-insulated bag and kept under a temperature range from 4° C. to 37° C.

The sample was then processed within 48 hours from time of collection.

Example 2: Isolation and Culture of Mesenchymal Stem Cells

First, veins and arteries of the umbilical cord were removed and followed by mincing into 1-2 mm fragments. The fragments were digested with an enzyme, preferably, but not limiting to 0.01% to 0.05% collagenase type II, for a period from 1 to 3 hours, forming a mixture. Next, a centrifugation was carried out to separate the mesenchymal stem cells from the mixture. The mesenchymal stem cells were isolated and then cultured in a growth medium, preferably, but not limiting to Dulbecco's Modified Eagle's Medium (DMEM) which may or may not contain low glucose supplemented with 5-20% animal-free serum and a combination of antibiotics comprising 100 U/mL penicillin, 100 mg/mL streptomycin, 250 ng/mL amphotericin B and 2 mM glutamine. The cultures were maintained at 37° C. in a humidified atmosphere of 5% $CO_2$ and 95% air for 3 days.

Non-adherent cells were discarded and the growth medium was replaced every 3-4 days until the cells reached confluence.

Next, the plastic-adherent mesenchymal stem cells were incubated with trypsin and re-plated at $1 \times 10^4$ cells/ml for 3-4 passages. The mesenchymal stem cells were then harvested in a culture flasks, thus expanding population of the cells.

Figure 1:
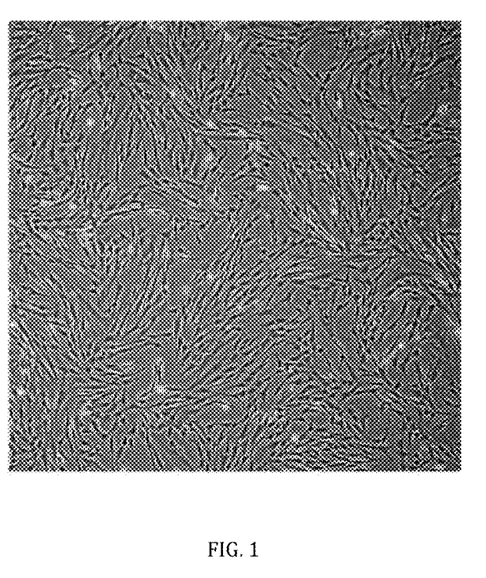
FIG. 1 illustrates morphology of human umbilical cord-derived mesenchymal stem cells.

FIG. 1 illustrates the morphology of the mesenchymal stem cells.

Example 3: Characterization of Mesenchymal Stem Cells

Immunophenotyping

Figure 2:
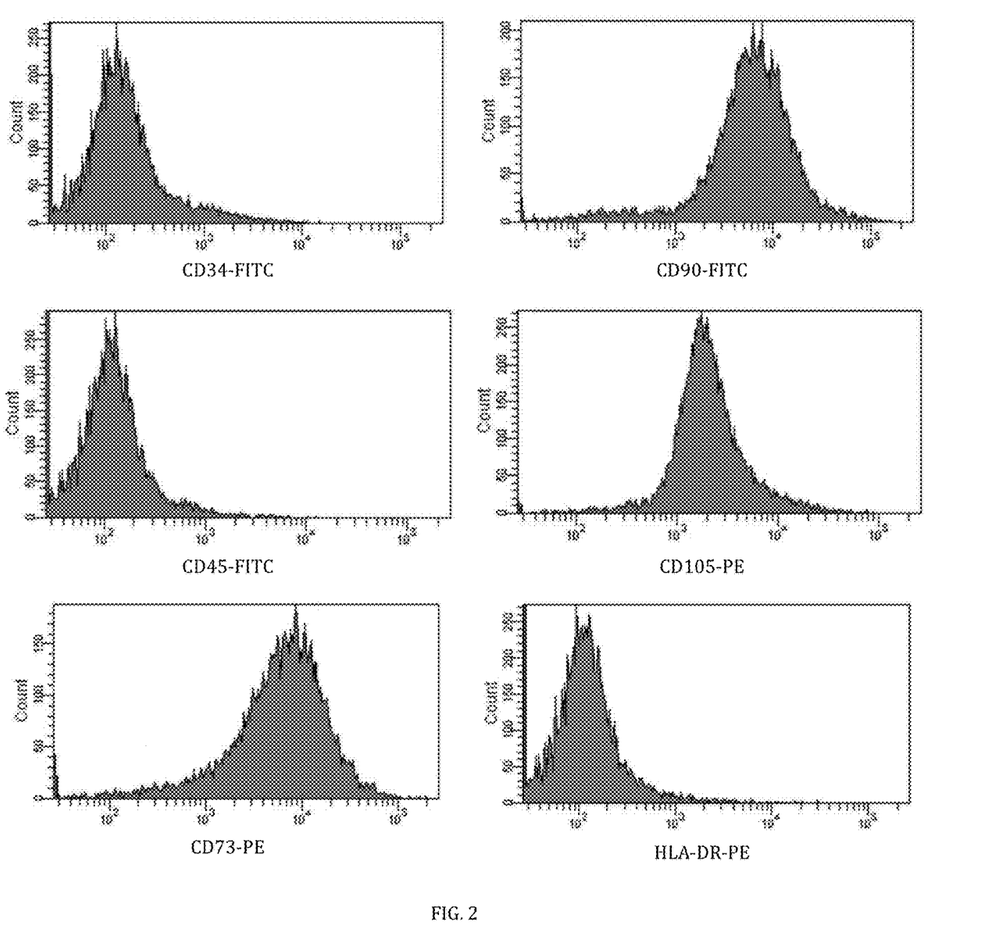
FIG. 2 illustrates immunophenotyping assay results of the mesenchymal stem cells.

The mesenchymal stem cells were immunophenotyped at passage three using isotype (fluorescein isothiocyanate) FITC and (phycoerythrin) PE controls with antigen markers which include CD34, CD45, CD73, CD90, CD105 and HLA-DR. As shown in FIG. 2, the immunophenotyping assay results for the mesenchymal stem cells validate expression for CD73, CD90 and CD105 whilst lacking expression for CD34, CD45 and HLA-DR.

Differentiation Assay

To perform this assay, a selection of specially formulated differentiation medium were used to induce tri-differentiation ability of the mesenchymal stem cells.

Adipogenesis:

The mesenchymal stem cells were treated in adipogenic differentiation medium comprising complete medium supplemented with 1 mM dexamethasone and 0.2 mM indomethacin, 0.01 mg/mL insulin and 0.5 mM 3-isobutil-1-metil-xantina. The medium was replaced every 3 days, and the differentiated cells were subjected to Oil Red O staining after about 14 days of culture.

Chondrogenesis:

The mesenchymal stem cells were cultured in pellet form and maintained in a chemically defined basal medium comprising complete medium supplemented with 50 mg/mL ascorbate-2-phosphate, 1.0 mM sodium piruvate, 40 mg/mL proline, 10 ng/mL transforming growth factor-b3, 6.25 mg/mL human insulin, 6.25 mg/mL transferrin, 6.25 mg/mL bovine insulin, 6.25 mg/mL selenous acid, 1.25 mg/mL linoleic acid, and 5.35 mg/mL bovine serum albumin. Next, the cells were suspended in 1 mL of chondrogenic medium and replaced every 3-4 days. Chondrogenic pellets were harvested after 5 weeks in culture. To assess chondrogenesis, Alcian Blue was used to stain cartilage matrix.

Osteogenesis:

The mesenchymal stem cells were treated in osteogenic differentiation medium comprising complete medium supplemented with 50 mg/mL ascorbate-2-phosphate, 10 mM b-glycerophosphate, and 100 nM dexamethasone. The medium was replaced every 3 days continuously for 2-3 weeks. Alizarin Red S was used to stain matrix mineralization associated with differentiated osteocytes.

Figure 3:
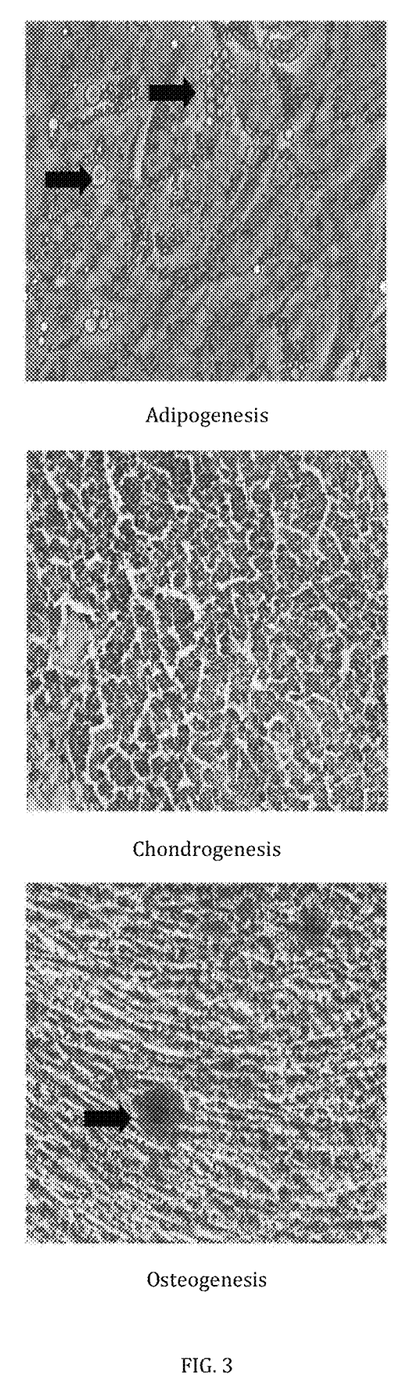
FIG. 3 illustrates adipogenesis, osteogenesis and chondrogenesis of the mesenchymal stem cells respectively.

FIG. 3 demonstrates the tri-differentiation ability of the mesenchymal stem cells exhibiting adipogenesis, osteogenesis and chondrogenesis respectively.

Example 4: Cryopreservation of Mesenchymal Stem Cells

Once the population of mesenchymal stem cells was expanded, trypsin was added in to the flasks and incubated at 37° C., for 5 minutes to detach the plastic-adherent mesenchymal stem cells, leaving the cells slightly shrunk. Next, the flasks were gently tapped to dislodge the cells and medium was further added to dilute the trypsin, forming a mesenchymal cell suspension. The cell suspension was then transferred into 50 ml centrifuge tubes and centrifuged at 500 g at a temperature ranging from 18° C. to 30° C. for 10 minutes forming a layer of supernatant with pellet at bottom of the tubes. The supernatant was removed, leaving the pellet of mesenchymal stem cells in the tubes.

The pellet of mesenchymal stem cells were re-suspended in a sterile cryovial containing cryopreservation medium comprising up to 90% animal-free serum and up to 10% dimethyl sulfoxide and were cryopreserved in a controlled freezing gradual rate at −90° C. before being transferred into a quarantine tank at −190° C.

Example 5: Preparation of the Cell-Based Composition for Treatment

The cryopreserved mesenchymal stem cells in cryovials were thawed at 37° C. in a water bath or an incubator for 2 minutes. Next, the cells were then transferred into new sterile cryovials and were washed with 0.9% sodium chloride. The washed cells in the sterile cryovials were then centrifuged at 800×g for 3-10 minutes at room temperature, forming a layer of supernatant and a pellet of mesenchymal stem cells. The supernatant was removed using a sterile syringe, leaving the pellet of mesenchymal stem cells in the cryovial.

The pellet of mesenchymal stem cells was then re-suspended with sterile saline at 10 ml, forming a suspension of mesenchymal stem cells. A cell-based composition was then prepared by infusing the suspension of mesenchymal stem cells into saline at a volume of 250 ml, in a sterile bottle.

Example 6: Treatment Procedure Using the Cell-Based Composition

Treatment using the cell-based composition was carried on 84 patients with established diabetes (Group A; 65 patients of whom 27 are poorly-controlled); and on fasting serum insulin (FSI) in pre-diabetic patients with insulin resistance (Group B; 19 patients). Diet, exercise and medications were not altered unless in medical emergencies. These patients were infused with a dose of the cell-based composition comprising a total number of cells from $50×10^6$ cells to $100×10^6$ cells over one or two sessions. Blood tests for FSI, glycated haemoglobin (Hba1c—marker of glycaemic control), high-sensitivity C-Reactive Protein (hs-CRP, marker of inflammation), fasting LDL cholesterol (LDL-Chol), triglyceride (TG), gamma-glutamyl transaminase and aspartate transaminase (GGT and AST, both markers of fatty liver infiltration) and serum creatinine (a marker of renal dysfunction) were measured at baseline and 6 months.

The treatment procedure began with infusion of 200 ml saline into the patients for a period from 45 to 60 minutes. Next, the cell-based composition which was prepared earlier (as described in Example 5) was infused into the patients for a period from 30 minutes to 2 hours. The bottle containing the cell-based composition was shaken gently every 5 minutes to ensure that the cells are suspended in saline homogenously. When the infusion is almost complete, 50 ml of sterile saline was infused into the bottle containing the cell-based composition to rinse and flush out any remaining cells.

Example 7: Results and Discussion

Patients were assessed for several metabolic function and blood pressure tests at baseline and 6 months after treatment.

All parametric data were presented as mean±SD. Comparison data between baseline and after 6 months follow-up were calculated using paired t-test. Data was analysed using Statistical Package for the Social Sciences (SPSS version 14.0) and $p<0.05$ is considered statistically significant.

Following infusion of the cell-based composition, it was found that all patients tolerated the procedure well. As shown in TABLE 1, in Group A, there was significant improvement of Hba1c (7.9±2.0 vs. 7.4±1.7%; p<0.001), Total-Cholesterol (4.7±1.4 vs. 4.2±1.0 mmol/L; p=0.01), LDL-Cholesterol (2.5±1.3 vs. 2.1±1.0 mmol/L; p=0.01) and Creatinine (107±115 vs. 97±93 umol/L; p=0.03). There were trends of improvement of hs-CRP, TG, AST and GGT. The reduction in Hba1c was most significant for poorly controlled diabetics (9.4±1.9 vs. 8.4±1.8%; p<0.001). In Group B, there was a significant reduction in FSI (38±26 vs. 9±4 uU/ml; p=0.03).

TABLE 1

Blood test and physical assessment at baseline and 6 months after receiving treatment in diabetes patients with Hba1c ≥6% (n = 65)

| Variables | Mean ± SD | | |
|---|---|---|---|
| | Baseline | After 6 months | p-value[a] |
| hsCRP (mg/L) | 35 ± 4.9 | 2.4 ± 3.5 | 0.16 |
| ESR (mm/hr) | 12 ± 12 | 14 ± 14 | 0.42 |
| Creatinine (μmol/L) | 107 ± 115 | 97 ± 93 | 0.03* |
| FBS (mmol/L) | 9.0 ± 4.6 | 8.3 ± 4.0 | 0.16 |
| Hba1c (%) | 7.9 ± 2.0 | 7.4 ± 1.7 | <0.001* |
| Total Testosterone (nmol/L)** | 10.3 ± 4.8 | 12.3 ± 6.0 | 0.03* |
| DHEA (μmol/L) | 3.1 ± 1.9 | 3.2 ± 2.1 | 0.90 |
| IGF-1 (ng/ml) | 164 ± 50 | 167 ± 62 | 0.70 |
| Serum Insulin (uU/ml) | 20 ± 20 | 21 ± 26 | 0.97 |
| Total cholesterol (mmol/L) | 4.7 ± 1.4 | 4.2 ± 1.0 | 0.01* |

TABLE 1-continued

Blood test and physical assessment at baseline and 6 months after receiving treatment in diabetes patients with Hba1c ≥6% (n = 65)

| Variables | Mean ± SD | | p-value[a] |
|---|---|---|---|
| | Baseline | After 6 months | |
| LDL cholesterol (mmol/L) | 2.5 ± 1.3 | 2.1 ± 1.0 | 0.01* |
| HDL cholesterol (mmol/L) | 1.2 ± 0.3 | 1.2 ± 0.4 | 0.21 |
| Triglycerides (mmol/L) | 2.2 ± 1.3 | 1.9 ± 1.2 | 0.06 |
| Total:HDL ratio | 4.1 ± 1.3 | 3.8 ± 1.2 | 0.06 |
| AST (IU/L) | 29 ± 17 | 25 ± 11 | 0.16 |
| ALT (IU/L) | 29 ± 14 | 26 ± 13 | 0.07 |
| GGT (IU/L) | 55 ± 112 | 43 ± 59 | 0.24 |
| Systolic BP (mmHg) | 144 ± 23 | 136 ± 22 | 0.16 |
| Dystolic BP (mmHg) | 84 ± 17 | 76 ± 11 | 0.07 |
| BMI (kg/m$^2$) | 26.7 ± 5.1 | 26.3 ± 4.5 | 0.21 |

[a]Paired t test
*Significant values, p < 0.05
**Serum Testosterone is only tested in male patients
Abbreviation:
hsCRP = high sensitive C-reactive protein;
ESR = erythrocyte sedimentation rate;
FBS = fasting blood sugar;
Hba1c = glycated hemoglobin;
DHEA = dehydroepiandrosterone;
IGF-1 = Insulin-like growth factor 1;
LDL = low-density lipoprotein;
HDL = high-density lipoprotein;
AST = aspartate transaminase;
ALT = alanine transaminase;
GGT = gamma-glutamyl transferase;
BP = blood pressure;
BMI = body mass index.

Figure 4:
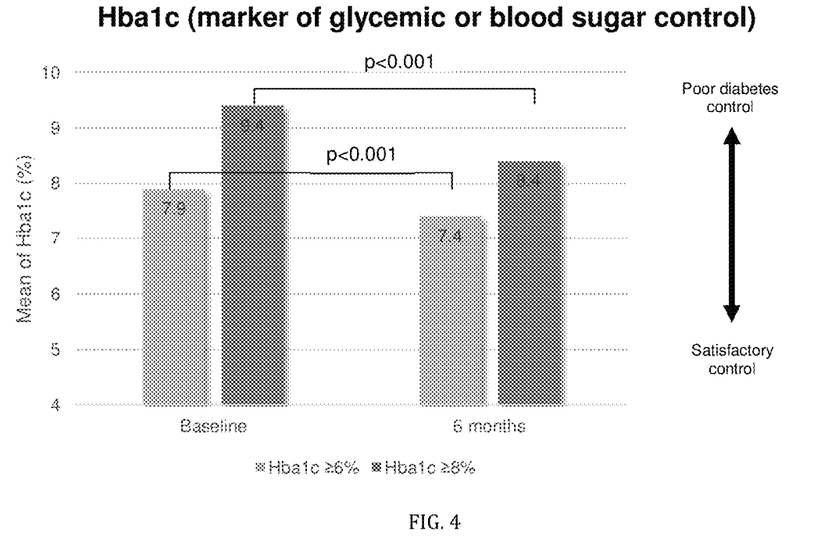
FIG. 4 illustrates mean of Hba1c at baseline and 6 months after receiving treatment using cell-based composition in all patients.

FIG. 4 illustrates mean of Hba1c at baseline and 6 months in all patients (Hba1c≥6%; n=65) and poorly controlled diabetics (Hba1c≥8%; n=27). Hba1c at baseline improved significantly after 6 months receiving treatment using cell-based composition for both groups (p<0.05, paired t-test).

Figure 5:
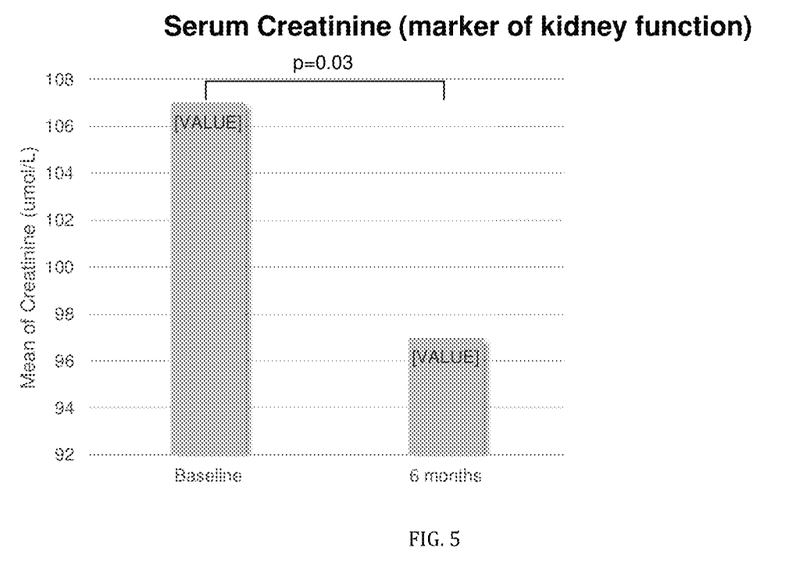
FIG. 5 illustrates mean of creatinine at baseline and 6 months after receiving treatment using cell-based composition in all patients.

Mean of creatinine at baseline and 6 months in all patients is indicated in FIG. 5. Creatinine at baseline improved significantly after 6 months receiving treatment using cell-based composition (p<0.05, paired t-test).

Figure 6:
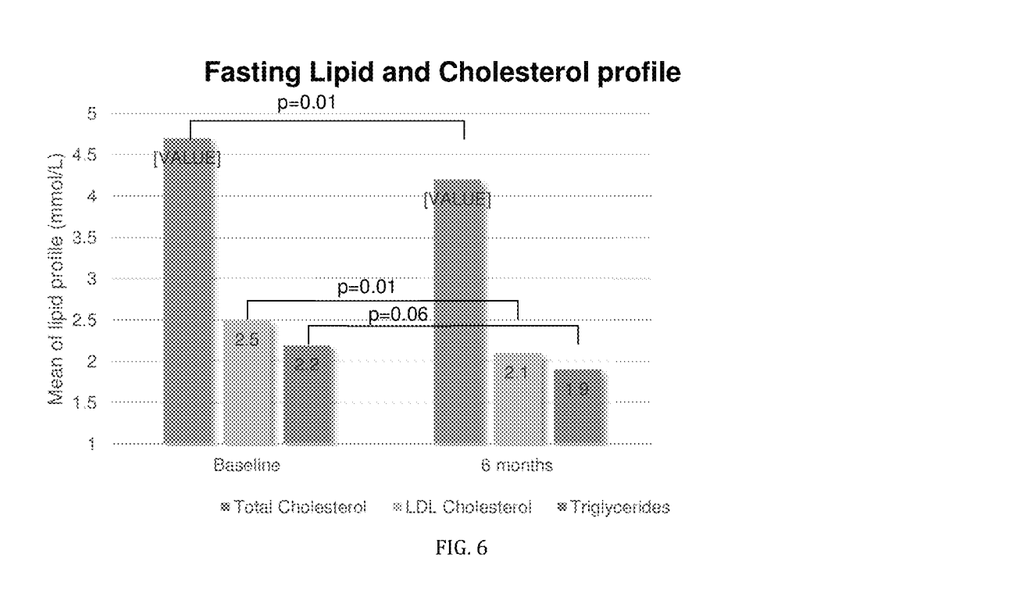
FIG. 6 illustrates lipid profile at baseline and 6 months after receiving treatment using cell-based composition in all patients.

Lipid profile at baseline and 6 months after in all patients (p<0.05, paired t-test) after receiving cell-based composition are as shown in FIG. 6 Mean of total cholesterol and LDL cholesterol showed significant reduction after 6 months receiving treatment (p<0.05, paired t-test).

Figure 7:
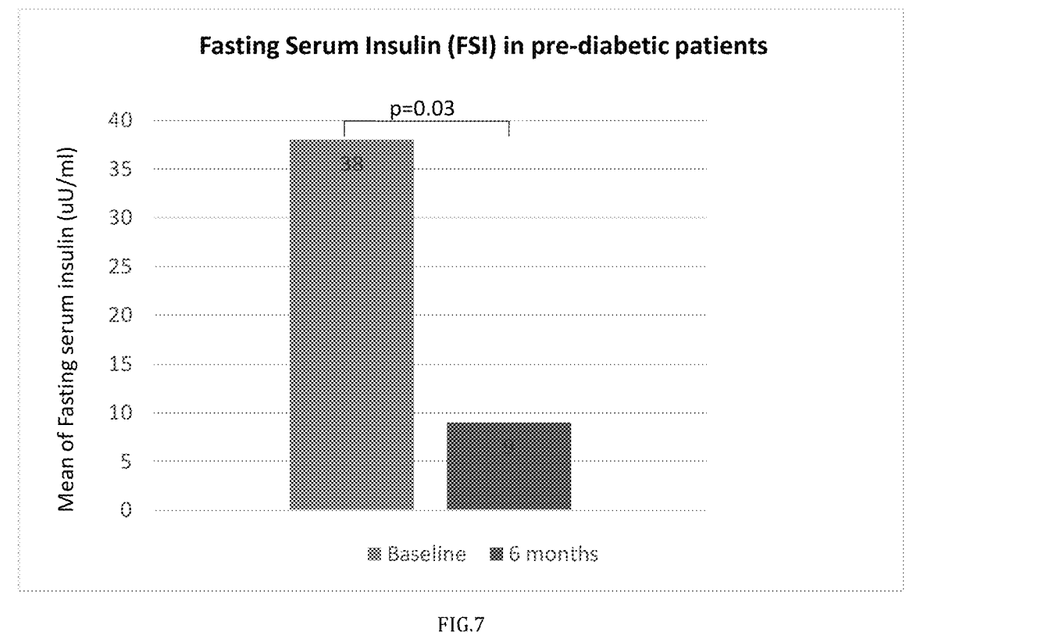
FIG. 7 illustrates mean of fasting serum insulin at baseline and 6 months after receiving treatment using cell-based composition in pre-diabetes patients.

FIG. 7 illustrates mean of fasting serum insulin at baseline and 6 months in pre-diabetes patients (FSI≥12 uU/ml; n=19). Fasting serum insulin at baseline improved and reduced significantly 6 months after infusion of the cell-based composition.

Based on the results above, treatment using cell-based composition has indicated improvement in metabolic functions of the patients which include cholesterol, renal functions and blood pressure. The results also demonstrated that infusion of the cell-based composition was able to ameliorate serum insulin resistance in pre-diabetics. Meanwhile, improvements in glycaemic control, renal dysfunction, fasting lipid profile and fatty liver infiltration in the patients were also observed.

Having described preferred embodiments of the present invention with reference to the accompanying drawings, it is not intended that these embodiments and examples illustrate and describe all possible forms of the present invention, and it is to be understood that the present invention is not limited to those precise embodiments, and that various changes and modifications may be effected therein by one skilled in the art without departing from the scope of the invention as defined in the appended claims.

The invention claimed is:

1. A method for the treatment of diabetes and its associated metabolic disorders and complications and for amelioration of insulin resistance in pre-diabetes in a human subject, said method comprising administering to said human subject a therapeutically effective amount of a cell-based composition consisting essentially of a suspension of mesenchymal stem cells in crystalloid with a cellular concentration from 0.01 million to 3.0 million cells/ml, wherein the therapeutically effective amount is from 0.25 million to 3.0 million cells/kg body weight.

2. The method as claimed in claim 1, wherein the administering step is carried out by intravenous infusion.

3. The method as claimed in claim 1, wherein the associated metabolic disorders and complications are selected from nephropathy, dyslipidaemia, diabetes foot ulcer, macular oedema, cardiomyopathy, and stroke.

4. The method as claimed in claim 2, wherein the intravenous infusion is carried out in a period ranging from 30 minutes to 2 hours.

5. A method for the treatment of diabetes and its associated metabolic disorders and complications and for amelioration of insulin resistance in pre-diabetes in a human subject, said method comprising administering to said human subject a therapeutically effective amount of a cell-based composition consisting essentially of a suspension of mesenchymal stem cells in crystalloid with a cellular concentration from 0.01 million to 3.0 million cells/ml, wherein the suspension of mesenchymal stem cells is derived from cryopreserved mesenchymal stem cells comprising from 25 to 35 million cells per cryovial and the therapeutically effective amount is from 0.25 million to 3.0 million cells/kg body weight.

6. The method as claimed in claim 5, wherein the administering step is carried out by intravenous infusion.

7. The method as claimed in claim 5, wherein the associated metabolic disorders and complications are selected from nephropathy, dyslipidaemia, diabetes foot ulcer, macular oedema, cardiomyopathy, and stroke.

8. The method as claimed in claim 6, wherein the intravenous infusion is carried out in a period ranging from 30 minutes to 2 hours.

9. A method for the treatment of diabetes and its associated metabolic disorders and complications and for amelioration of insulin resistance in pre-diabetes in a human subject, said method comprising administering to said human subject a therapeutically effective amount of a cell-based composition consisting essentially of a suspension of mesenchymal stem cells in crystalloid with a cellular concentration from 0.01 million to 3.0 million cells/ml, wherein the suspension of mesenchymal stem cells is derived from human umbilical cord, bone marrow, fat tissue, peripheral blood, or tooth pulp and the therapeutically effective amount is from 0.25 million to 3.0 million cells/kg body weight.

10. The method as claimed in claim 9, wherein the administering step is carried out by intravenous infusion.

11. The method as claimed in claim 9, wherein the associated metabolic disorders and complications are selected from nephropathy, dyslipidaemia, diabetes foot ulcer, macular oedema, cardiomyopathy, and stroke.

12. The method as claimed in claim 10, wherein the intravenous infusion is carried out in a period ranging from 30 minutes to 2 hours.

13. A method for the treatment of diabetes and its associated metabolic disorders and complications and for amelioration of insulin resistance in pre-diabetes in a human subject, said method comprising administering to said human subject a therapeutically effective amount of a cell-based composition consisting essentially of a suspension of mesenchymal stem cells in crystalloid with a cellular concentration from 0.01 million to 3.0 million cells/ml, wherein the suspension of mesenchymal stem cells is positive for a selected group of surface markers including CD73, CD90, and CD105, and negative for a selected group of surface markers including CD34, CD45, and HLA-DR and the therapeutically effective amount is from 0.25 million to 3.0 million cells/kg body weight.

14. The method as claimed in claim 13, wherein the administering step is carried out by intravenous infusion.

15. The method as claimed in claim 13, wherein the associated metabolic disorders and complications are selected from nephropathy, dyslipidaemia, diabetes foot ulcer, macular oedema, cardiomyopathy, and stroke.

16. The method as claimed in claim 14, wherein the intravenous infusion is carried out in a period ranging from 30 minutes to 2 hours.

\* \* \* \* \*

UNITED STATES PATENT AND TRADEMARK OFFICE
CERTIFICATE OF CORRECTION

PATENT NO. : 11,052,119 B2
APPLICATION NO. : 16/284177
DATED : July 6, 2021
INVENTOR(S) : Bernard Sze-Piaw Chin et al.

It is certified that error appears in the above-identified patent and that said Letters Patent is hereby corrected as shown below:

On the Title Page

Please delete the Title Page and insert the attached Title Page showing the corrected illustrative figure.

In the Drawings

Please replace Figs 4-5 with Figs 4-5 as shown on the attached page.

Please replace Figs 6-7 with Figs 6-7 as shown on the attached page.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*

(12) United States Patent
Chin et al.

(10) Patent No.: US 11,052,119 B2
(45) Date of Patent: Jul. 6, 2021

(54) CELL-BASED COMPOSITION AND USE THEREOF FOR TREATMENT OF DIABETES AND ASSOCIATED METABOLIC DISORDERS AND FOR AMELIORATION OF INSULIN RESISTANCE IN PRE-DIABETES

(71) Applicant: Cytopeutics Sdn. Bhd., Selangor (MY)

(72) Inventors: Bernard Sze-Piaw Chin, Selangor (MY); Kong Yong Then, Selangor (MY); Soon Keng Cheong, Selangor (MY)

(73) Assignee: Cytopeutics Sdn. Bhd., Selangor (MY)

(*) Notice: Subject to any disclaimer, the term of this patent is extended or adjusted under 35 U.S.C. 154(b) by 177 days.

(21) Appl. No.: 16/284,177

(22) Filed: Feb. 25, 2019

(65) Prior Publication Data
US 2019/0209620 A1    Jul. 11, 2019

Related U.S. Application Data

(62) Division of application No. 15/597,725, filed on May 17, 2017, now abandoned.

(30) Foreign Application Priority Data

May 25, 2016    (MY) .......................... PI 2016701900

(51) Int. Cl.
*A61K 35/28*    (2015.01)
*C12N 5/0775*    (2010.01)

(52) U.S. Cl.
CPC ............ *A61K 35/28* (2013.01); *C12N 5/0665* (2013.01)

(58) Field of Classification Search
None
See application file for complete search history.

(56) References Cited

U.S. PATENT DOCUMENTS

2007/0269887 A1    11/2007  Coelho et al.
2012/0201791 A1    8/2012   Yoo
2015/0086514 A1*   3/2015   Huang .............. A61P 3/10
                                              424/93.7

OTHER PUBLICATIONS

Cortes, D. Orbegozo; et al; "Isotonic crystalloid solutions: a structured review of the literature" British Journal of Anaesthesia, 112; 968-981, 2014 (Year: 2014).*
Jong, Renate de; "Advanced Cell-Based Cardiac Repair: How to Mend a Broken Heart" Thesis, Erasmus University Medical Center, 2014 (Year: 2014).*
Al-Saqi et al "Defined Serum- and Xeno-Free Cryopreservation of Mesenchymal Stem Cells" Cell Tissue Bank vol. 16, pp. 181-193, 2015.
Chhabra et al "Challenges in the Management of Type 2 Diabetes Mellitus and Cardiovascular Risk Factors in Obese Subjects: What is the Evidence and What are the Myths?" International Journal of Endocrinology vol. 2013, pp. 1-10, 2013.
(Continued)

*Primary Examiner* — David W Berke-Schlessel
(74) *Attorney, Agent, or Firm* — Cesari & McKenna, LLP

(57)    ABSTRACT

The present invention relates to a cell-based composition comprising a suspension of mesenchymal stem cells in crystalloid with a cellular concentration from 0.01 million to 3.0 million cells/ml. The cell-based composition is used in a form of medicament for treatment of diabetes and its associated metabolic disorders and complications.

16 Claims, 5 Drawing Sheets

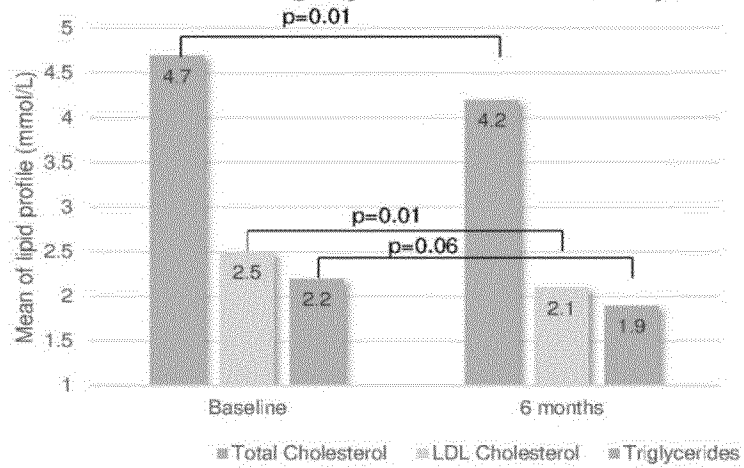

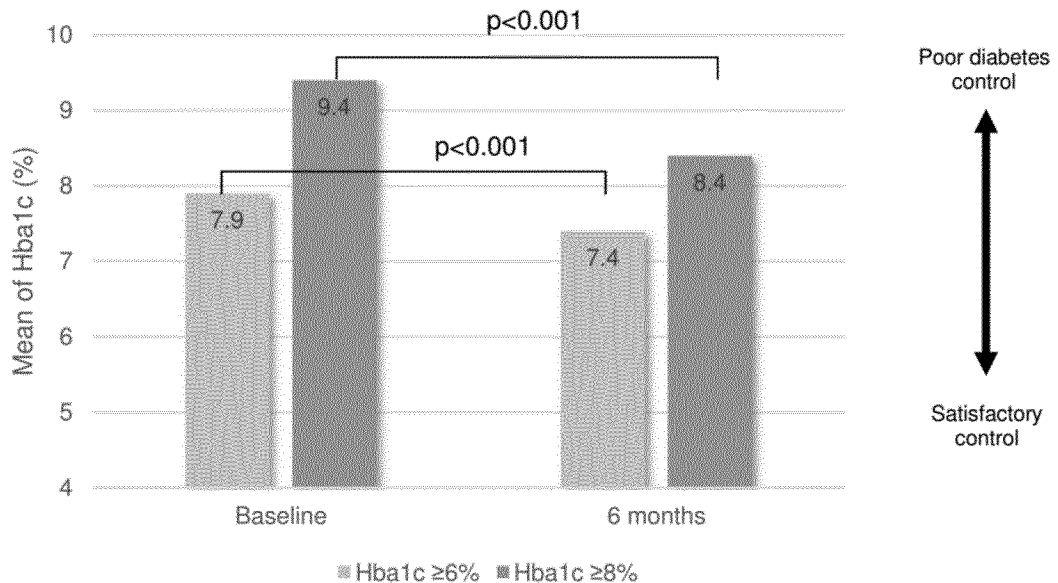
FIG. 4
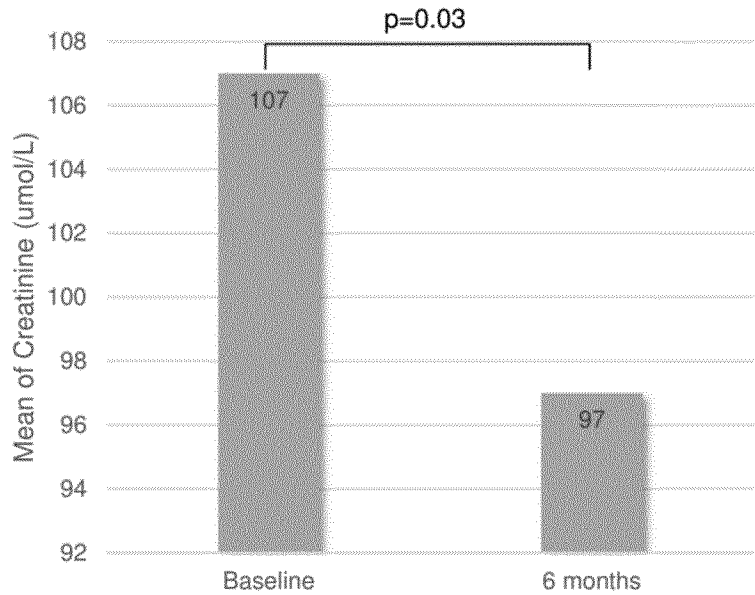
FIG. 5

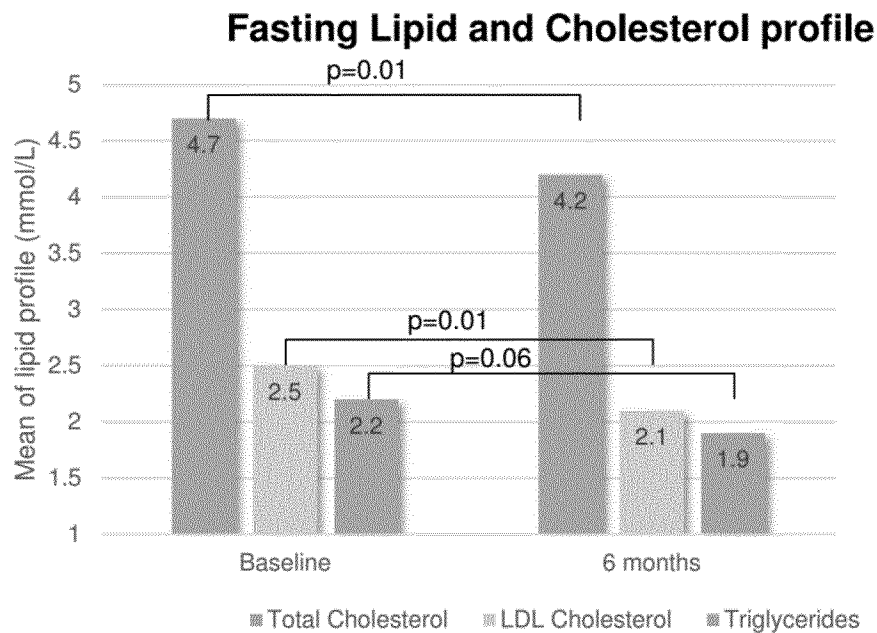
FIG. 6
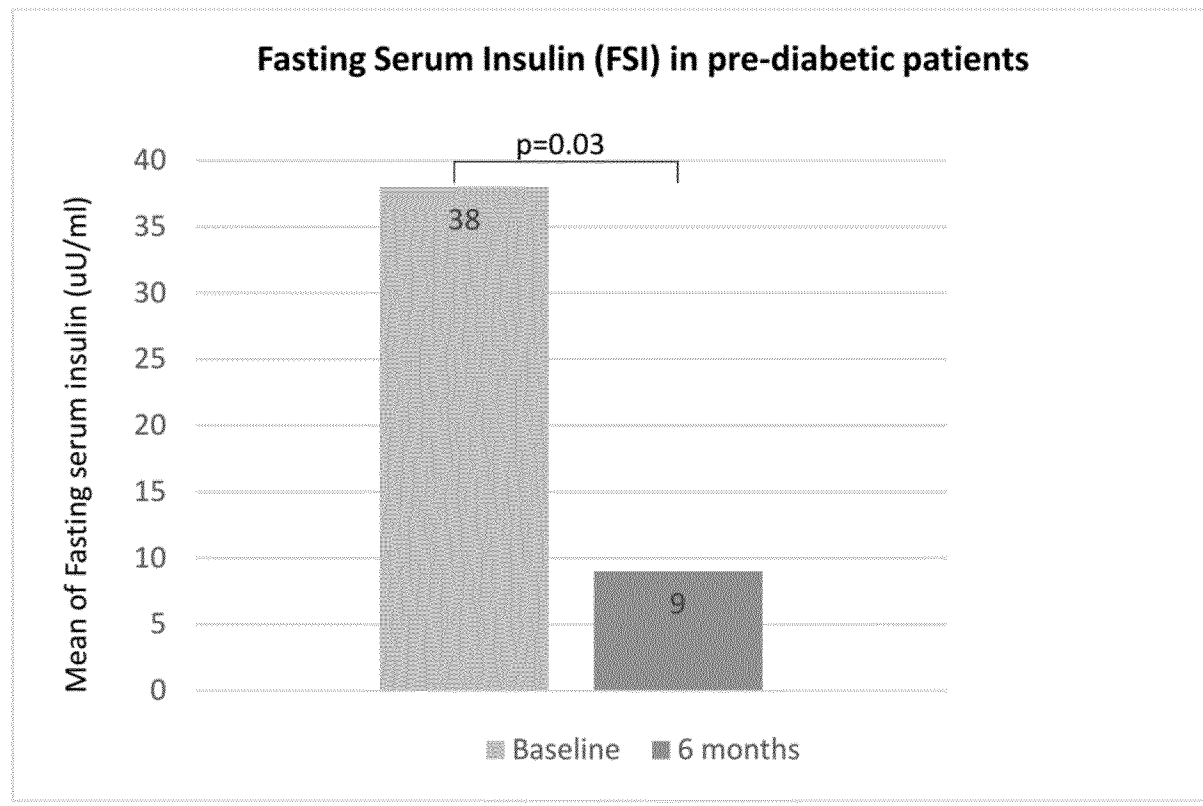
FIG. 7